US012098401B2

(12) United States Patent
Lee et al.

(10) Patent No.: US 12,098,401 B2
(45) Date of Patent: Sep. 24, 2024

(54) FRUCTOSE-4-EPIMERASE AND METHOD FOR PREPARING TAGATOSE USING SAME

(71) Applicant: CJ CHEILJEDANG CORPORATION, Seoul (KR)

(72) Inventors: Young Mi Lee, Seoul (KR); Il Hyang Park, Seoul (KR); Seong Bo Kim, Seoul (KR); Seung Won Park, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 721 days.

(21) Appl. No.: 17/281,229

(22) PCT Filed: Aug. 9, 2019

(86) PCT No.: PCT/KR2019/010091
§ 371 (c)(1),
(2) Date: Mar. 29, 2021

(87) PCT Pub. No.: WO2020/080658
PCT Pub. Date: Apr. 23, 2020

(65) Prior Publication Data
US 2022/0372534 A1    Nov. 24, 2022

(30) Foreign Application Priority Data
Oct. 19, 2018  (KR) .................. 10-2018-0125279

(51) Int. Cl.
*C12P 19/02*   (2006.01)
*C12N 1/21*    (2006.01)
*C12N 9/90*    (2006.01)
*C12P 19/24*   (2006.01)

(52) U.S. Cl.
CPC ............... *C12P 19/02* (2013.01); *C12N 9/90* (2013.01); *C12P 19/24* (2013.01); *C12Y 501/03002* (2013.01)

(58) Field of Classification Search
None
See application file for complete search history.

(56) References Cited

FOREIGN PATENT DOCUMENTS

| KR | 10-0964091 B1 | 6/2010 | | |
|---|---|---|---|---|
| KR | 10-1368731 B1 | 3/2014 | | |
| KR | 10-1480422 B1 | 1/2015 | | |
| KR | 10-2014-0133680 A | 4/2016 | | |
| KR | 10-2016-0047361 A | 5/2016 | | |
| KR | 10-2018-0004024 A | 1/2018 | | |
| KR | 10-2018-0027962 A | 3/2018 | | |
| KR | 10-2018-0111678 A | 10/2018 | | |
| KR | 10-2076288 B1 | 2/2020 | | |
| WO | WO 2006/058092 A2 | 6/2006 | | |
| WO | WO-2016064146 A1 | * | 4/2016 | ........... C07K 14/195 |
| WO | WO-2018182355 A1 | * | 10/2018 | ............. C12N 15/52 |
| WO | WO 2020/010260 A1 | 1/2020 | | |

OTHER PUBLICATIONS

GenBank, Accession No. OUC05982, 2017, www.ncbi.nlm.nih. gov. (Year: 2017).*
Wichelecki et al., ATP-binding Cassette (ABC) Transport System Solute-binding Protein-guided Identification of Novel D-Altritol and Galactitol Catabolic Pathways in Agrobacterium tumefaciens C58, J. Biol. Chem. 290, 2015, 28693-76. (Year: 2015).*
International Search Report and Written Opinion of PCT/KR2019/010091 mailed Nov. 29, 2019 together with the English translation of the international search report (total of 10 pages).
GenBank accession No. OUC05982.1, hypothetical protein RY27_23815 [Litorilinea aerophila] May 17, 2017.
Communication pursuant to Article 94(3) EPC of EP Application No. 19873002.0 dated Aug. 19, 2022; 4 pages.
Kale et al., "*Litorilinea aerophila* gen. nov., sp. nov., an aerobic member of the class Caldilineae, phylum Chloroflexi, isolated from an intertidal hot spring", International Journal of Systematic and Evolutionary Microbiology, 2013, 63, pp. 1149-1154; DOI 10.1099/ijs.0.044115-0.
Extended European Search report of EP application No. 19873002.0 dated Oct. 27, 2021; 8 pages.
Anonymous: "D-tagatose-1,6-bisphosphate aldolase subunit GatZ/KbaZ-like", Jul. 27, 2017, XP055851842; Database accession No. OUC05982.

* cited by examiner

*Primary Examiner* — Todd M Epstein
(74) *Attorney, Agent, or Firm* — Squire Patton Boggs (US) LLP

(57) ABSTRACT

The present disclosure relates to a fructose-C4-epimerase and a method of preparing tagatose using the same.

8 Claims, 2 Drawing Sheets

Specification includes a Sequence Listing.

SEQUENCE LISTING

<160> NUMBER OF SEQ ID NOS: 2

<210> SEQ ID NO 1
<211> LENGTH: 431
<212> TYPE: PRT
<213> ORGANISM: Unknown
<220> FEATURE:
<223> OTHER INFORMATION: Litorilinea aerophila

<400> SEQUENCE: 1

Met Tyr Pro Val Leu Glu Asn Ile Leu Arg Ala Gln Gln Gln Gly Glu
1               5                   10                  15

Ala Leu Gly Ile Pro Ser Ile Cys Ser Ala His Pro Phe Val Leu Glu
            20                  25                  30

Ala Thr Phe Arg His Ala Leu Thr Thr Gly Arg Thr Val Leu Ile Glu
        35                  40                  45

Ser Thr Cys Asn Gln Val Asn Gln His Gly Gly Tyr Thr Gly Met Thr
    50                  55                  60

Pro Gly Asp Phe Val Ala Tyr Val Ala Ala Leu Ala Asp Arg Leu His
65                  70                  75                  80

Phe Pro Arg Glu Arg Ile Leu Leu Gly Gly Asp His Leu Gly Pro Asn

|  |  |  |  | 85 |  |  |  |  | 90 |  |  |  |  | 95 |  |
|---|---|---|---|---|---|---|---|---|---|---|---|---|---|---|---|

Pro Trp Arg Asp Arg Pro Ala Asp Gln Ala Leu Asn Gln Ala Arg Ile
                100                 105                 110

Leu Val Gln Glu Tyr Val Arg Ala Gly Tyr Gly Lys Ile His Leu Asp
        115                 120                 125

Ala Ser Met Ala Cys Gly Gly Asp Pro Ala Asp Ala Pro Leu Asp Lys
    130                 135                 140

Ala Val Ala Ala Glu Arg Ala Ala Leu Ala Glu Ala Ala Glu Ala
145                 150                 155                 160

Ala Phe Gln Arg Met Gly Ser Gly Thr Pro Pro Cys Tyr Val Ile Gly
                165                 170                 175

Thr Glu Val Pro Pro Gly Gly Ala Gln Gly Asp Asp Met Pro Leu
            180                 185                 190

Ala Ile Thr Ala Pro Arg Glu Val Ala Glu Thr Ile Glu Leu Thr Gln
    195                 200                 205

Ala Ala Phe Arg Arg Arg Gly Leu Glu Ala Ala Trp Glu Arg Val Ile
    210                 215                 220

Ala Val Val Val Gln Pro Gly Val Glu Phe Gly Asp Glu Gln Val His
225                 230                 235                 240

Pro Tyr Asp Arg Ala Ala Ala Gly Leu Ala Arg Ala Ile Glu Pro
                245                 250                 255

Tyr Gly Arg Leu Val Tyr Glu Ala His Ser Thr Asp Tyr Gln Thr Arg
            260                 265                 270

Gln Ala Leu Arg Asp Leu Val Ala Asp His Phe Ala Ile Leu Lys Val
        275                 280                 285

Gly Pro Ala Leu Thr Phe Ala Phe Arg Glu Ala Val Phe Ala Leu Ala
    290                 295                 300

Ala Val Glu Glu Glu Trp Leu Ala Gly Gln Ala Gly Val Val Leu Ser
305                 310                 315                 320

Arg Leu Arg Glu Glu Leu Glu Ala Ala Met Ile Gln Asp Pro Thr His
                325                 330                 335

Trp Arg Gly Tyr Tyr Arg Gly Asp Glu Arg His Gln Arg Leu Ala Arg
            340                 345                 350

Arg Tyr Ser Tyr Ser Asp Arg Ala Arg Tyr Tyr Trp Pro Arg Pro Ser
        355                 360                 365

Val Gln Ala Ala Leu Glu Arg Leu Leu His Asn Leu Glu Ala Ala Pro
    370                 375                 380

Pro Pro Leu Thr Leu Leu Ser Gln Tyr Leu Pro Val Gln Tyr Trp Ser
385                 390                 395                 400

Val Arg Glu Gly Leu Leu Glu Pro Thr Pro Arg Ser Leu Ile Val Asp
                405                 410                 415

Lys Ile Ile Gln Val Leu Asn Asp Tyr Thr Trp Ala Cys Gly Gly
            420                 425                 430

<210> SEQ ID NO 2
<211> LENGTH: 1296
<212> TYPE: DNA
<213> ORGANISM: Unknown
<220> FEATURE:
<223> OTHER INFORMATION: Litorilinea aerophila

<400> SEQUENCE: 2 atgtacccg tcctggaaaa catcctgcgc gcccagcagc agggcgaagc cctgggcatc      60
ccgtccatct gctccgcgca ccctttgtg ctggaggcga ctttccgcca cgccctgacc     120

```
accggccgga ccgtgctcat tgaatccacc tgcaaccagg tgaaccagca cggcggatac    180
acgggcatga cgcccggtga ctttgtggcc tacgtggccg ccctggccga tcggctccac    240
tttccccgag aacgcatcct gttgggtggc gatcacctgg ggcccaaccc ctggcgggat    300
cgcccggcgg accaggccct gaaccaggcc cggatcctgg tccaggaata tgtacgggcc    360
ggctacggca agatccacct ggacgcgagc atggcctgtg gcggggatcc agccgacgcc    420
cccctggaca aagccgtggc ggccgagcgg gccgcagccc tggccgaggc agcggaagcc    480
gcgtttcaac ggatggggag tggaacgccc ccctgctacg tcatcggcac ggaggtgcca    540 ccccgggcg gcgcccaggg agacgacatg cccctggcca tcaccgcgcc ccgggaagtg    600
gccgagacca tcgagctgac ccaggcagcc ttccgccggc gcgggctgga agcagcctgg    660
gaacgggtca ttgcggtggt ggtgcagcca ggcgtggagt tcggcgacga gcaggtgcat    720
ccatatgacc gggctgcggc ggccggcctg gcccgggcca tcgagcccta cgggcggctg    780
gtgtacgagg cccactccac cgactaccag acccgccagg ccctgcggga tctggtggcg    840
gatcactttg ccatcctgaa ggtggggccg gccctcactt ttgcctttcg ggaggcggtc    900
tttgccctgg ctgcggtgga ggaggaatgg ctggccggcc aggcgggggt ggtcctgtcc    960
cggctgcggg aggagctgga ggcagccatg atccaggatc ccacccactg gcggggctat   1020
tatcgagggg atgagcggca tcaacgattg gctcgccgct acagctacag cgaccgggcc   1080
cgctactatt ggccacggcc gtccgtccag gcggcgctgg aacggctgct acacaacctg   1140
gaggccgccc cgccgcccct gaccctgctc agccaatacc tgcctgtgca gtactggagc   1200
gtccgcgaag ggctcctgga gccgacgccc cggtccctga tcgtggacaa aatcatccag   1260
gtgttgaatg actacacctg ggcctgtggg ggatga                             1296
```

FRUCTOSE-4-EPIMERASE AND METHOD FOR PREPARING TAGATOSE USING SAME

This application includes an electronically submitted sequence listing in .txt format. The .txt file contains a sequence listing entitled "059520_00023_ST25_ Sequence_ Listing.txt" created on Mar. 29, 2021 and is 6 KB in size. The sequence listing contained in this .txt file is part of the specification and is hereby incorporated by reference herein in its entirety.

TECHNICAL FIELD

The present disclosure relates to a novel fructose-C4-epimerase and a method of preparing tagatose using the same.

BACKGROUND ART

Tagatose is a natural sweetener, which is present in a small amount in food, such as milk, cheese, and cacao, and sweet fruits, such as apples and mandarin. Although tagatose has an energy value of 1.5 kcal/g, about one third of that of sucrose, and a glycemic index (GI) of 3, about 5% of that of sucrose, physical properties and taste of tagatose are similar to those of sucrose and tagatose has various functions beneficial to health. Therefore, tagatose may be used as a sugar substitute satisfying both health and taste.

Tagatose has been prepared using galactose as a main ingredient by a method well known or commonly used in the art such as a chemical method (catalytic reaction) and a biological method (isomerizing enzyme reaction) (PCT WO2006/058092, and Korean Patent Nos. 10-0964091 and 10-1368731). However, it is difficult to stably supply lactose which has been used as a raw material of galactose, used a main ingredient of tagatose in conventional preparation methods, because the price of lactose fluctuates in accordance with yields, demands, and supplies of raw milk and lactose. Therefore, there is a need to develop methods of preparing tagatose using a common sugar (e.g., sucrose, glucose, fructose, and the like) as a raw material.

DESCRIPTION OF EMBODIMENTS

Technical Problem

As a result of intensive researches to develop enzymes having activity for converting fructose into tagatose, the present inventors have found that a polypeptide sequence whose function has not been revealed yet has fructose-C4-epimerase activity and have confirmed that the found polypeptide has fructose-C4-epimerase activity for converting fructose into tagatose, thereby completing the present disclosure.

Solution to Problem

An object of the present disclosure is to provide a polypeptide having fructose-C4-epimerase activity and including an amino acid sequence of SEQ ID NO: 1.

Another object of the present disclosure is to provide a composition for producing tagatose including at least one of: the polypeptide; a microorganism expressing the polypeptide; or cultures of the microorganism.

Still another object of the present disclosure is to provide a microorganism including at least one of the polypeptide having fructose-C4-epimerase activity, a polynucleotide encoding the polypeptide, and an expression vector including the polynucleotide.

Still another object of the present disclosure is to provide a method of preparing tagatose including converting fructose into tagatose by contacting the composition with fructose.

Still another object of the present disclosure is to provide a use of a polypeptide including an amino acid sequence of SEQ ID NO: 1 or an amino acid sequence having at least 85% homology or identity with SEQ ID NO: 1, as fructose-C4-epimerase.

Advantageous Effects of Disclosure

Fructose-C4-epimerase according to the present disclosure enables industrial production of tagatose due to excellent heat resistance and is economically feasible by converting fructose, as a common sugar, into tagatose.

BEST MODE

Figure 1:
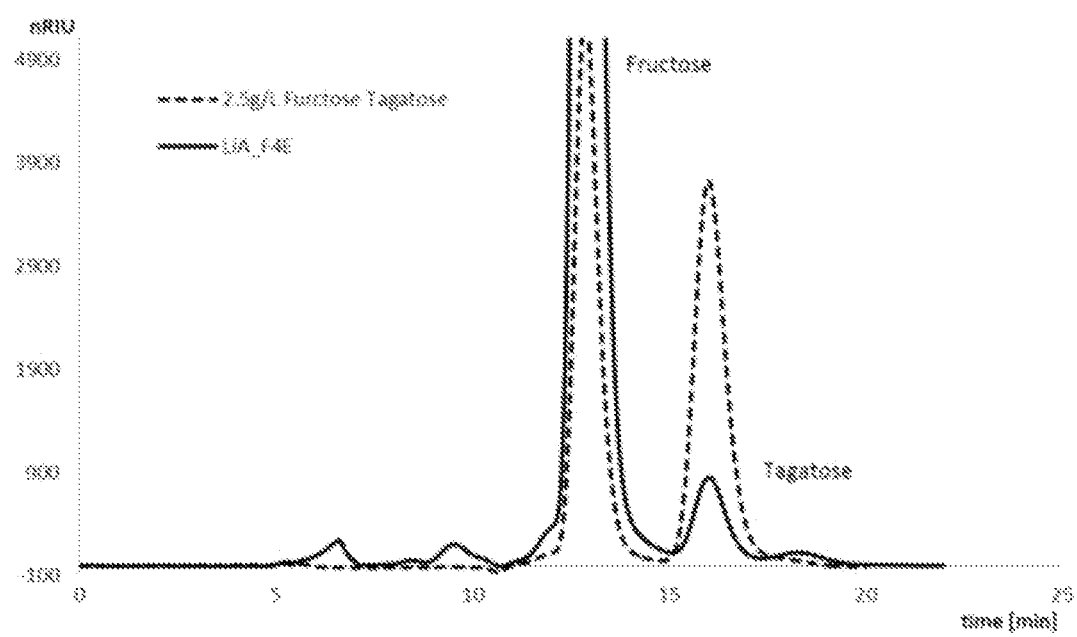
FIG. 1 is a high-performance liquid chromatography (HPLC) graph of fructose-C4-epimerase activity of CJ_LiA_F4E, as a hypothetical protein.

Hereinafter, the present disclosure will be described in detail. Meanwhile, each description and embodiment disclosed in the present disclosure may be applied herein to describe different descriptions and embodiments. In other words, all combinations of various components disclosed in the present disclosure are included within the scope of the present disclosure. Furthermore, the scope of the present disclosure should not be limited by the detailed descriptions provided below.

Those skilled in the art will recognize, or be able to ascertain, using no more than routine experimentation, many equivalents to specific embodiments of the present disclosure. Such equivalents are intended to be encompassed in the scope of the present disclosure.

An aspect of the present disclosure to achieve the above objects provides a polypeptide having fructose-C4-epimerase activity and including an amino acid sequence of SEQ ID NO: 1.

Another aspect of the present disclosure provides a composition for producing tagatose including at least one of: a polypeptide having fructose-C4-epimerase activity and including an amino acid sequence of SEQ ID NO: 1; a microorganism expressing the polypeptide; or cultures of the microorganism.

According to the present disclosure, it has been found that the polypeptide (protein) having the amino acid sequence of SEQ ID NO: 1 has fructose-C4-epimerase activity.

The fructose-C4-epimerase has a characteristic of epimerizing D-fructose at C4 to convert the D-fructose into D-tagatose.

The present inventors have found that the polypeptide having the amino acid sequence of SEQ ID NO: 1 has fructose-C4-epimerase activity. Thus, an embodiment of the present disclosure provides a novel enzymatic use of the polypeptide having fructose-C4-epimerase activity and including the amino acid sequence of SEQ ID NO: 1, known as a hypothetical protein, in preparation of tagatose from fructose. Another embodiment of the present disclosure provides a method of preparing tagatose from fructose using the polypeptide having fructose-C4-epimerase activity and including the amino acid sequence of SEQ ID NO: 1.

The polypeptide having fructose-C4-epimerase activity according to the present disclosure may also include a polypeptide having a sequence having at least 70% homology or identity with the amino acid sequence of SEQ ID NO: 1 capable of producing tagatose using fructose as a substrate without limitation. Particularly, fructose-C4-epimerase may have a conversion rate, from fructose, as a substrate, to tagatose, of 0.01% or greater, preferably 0.1% or greater, and more preferably 0.3% or greater (conversion rate=weight of tagatose/initial weight of fructose ×100). More particularly, the conversion rate may be in the range of 0.01% to 40%, in the range of 0.1% to 30%, in the range of 0.3% to 25%, or in the range of 0.3% to 20%.

The polypeptide having fructose-C4-epimerase activity according to the present disclosure may be an enzyme having fructose-C4-epimerase activity and derived from a heat-resistant microorganism or a variant thereof, for example, an enzyme derived from a microorganism belonging to *Litorilinea* sp. or a variant thereof, but are not limited thereto. Particularly, the polypeptide may be an enzyme derived from *Litorilinea aerophila* or a variant thereof.

The polypeptide having fructose-C4-epimerase activity according to the present disclosure may be an enzyme with excellent heat resistance. Particularly, the polypeptide having fructose-C4-epimerase activity according to the present disclosure may exhibit an activity of 50% to 100%, 60% to 100%, 70% to 100%, or 75% to 100% of the maximum activity at a temperature of 30° C. to 70° C. More particularly, the polypeptide having fructose-C4-epimerase activity according to the present disclosure may exhibit an activity of 80% to 100% or 85% to 100% of the maximum activity at a temperature of 40° C. to 70° C., 40° C. to 65° C., 45° C., 50° C., 55° C., or 60° C. Furthermore, the polypeptide having fructose-C4-epimerase activity and consisting of the sequence of SEQ ID NO: 1 may be encoded by a nucleotide sequence of SEQ ID NO: 2 without being limited thereto.

Particularly, the polypeptide having fructose-C4-epimerase activity according to the present disclosure may include an amino acid sequence having at least 85% identity with SEQ ID NO: 1. As another example, the polypeptide having fructose-C4-epimerase activity may include a polypeptide consisting of the amino acid sequence of SEQ ID NO: 1 or a polypeptide having at least 70%, 80%, 90%, 95%, 97%, or 99% homology or identity with SEQ ID NO: 1. In addition, it will be obvious that any polypeptide having an amino acid sequence including a deletion, a modification, a substitution, or an addition of one or several amino acids is within the scope of the present disclosure, as long as the polypeptide has an amino acid sequence retaining the homology or identity and an effect corresponding to the protein consisting of the amino acid sequence of SEQ ID NO: 1 (i.e., fructose-C4-epimerase activity for converting fructose into tagatose by epimerizing the fructose at C4). The polypeptide according to the present disclosure may also include, without limitation, any polypeptide having fructose-C4-epimerase activity and encoded by a probe prepared using any known gene sequence, e.g., a polynucleotide hybridized with a nucleotide sequence entirely or partially complementary to the nucleotide sequence encoding the polypeptide according to the present disclosure under stringent conditions. The composition may further include at least one polypeptide having fructose-C4-epimerase activity and including an amino acid sequence having at least 85% identity with SEQ ID NO: 1.

In other words, it will be obvious that any protein having an amino acid sequence including a deletion, a modification, a substitution, a conservative substitution, or an addition of one or several amino acids may also be used in the present disclosure, as long as the protein has activity identical or similar to that of the polypeptide having the amino acid sequence of the present disclosure, although it is disclosed as 'a protein or polypeptide including an amino acid sequence set forth in a predetermined SEQ ID NO:', 'a protein or polypeptide consisting of an amino acid sequence set forth in a predetermined SEQ ID NO', or 'a protein or polypeptide having an amino acid sequence set forth in a predetermined SEQ ID NO:'. Examples thereof may include an addition of a sequence to the N-terminal and/or the C-terminal of the amino acid sequence without causing changes in functions of the protein, naturally occurring mutants, and a silent mutation or a conservative substitution thereof.

The term "conservative substitution" refers to a substitution of one amino acid with another amino acid having a similar structural and/or chemical property. Such an amino acid substitution may generally occur based on similarity of polarity, charge, solubility, hydrophobicity, hydrophilicity, and/or amphipathic nature of a residue. For example, positively charged (basic) amino acids include arginine, lysine, and histidine; negatively charged (acidic) amino acids include glutamic acid and aspartic acid; aromatic amino acids include phenylalanine, tryptophan, and tyrosine, and hydrophobic amino acids include alanine, valine, isoleucine, leucine, methionine, phenylalanine, tyrosine, and tryptophan.

Another aspect of the present disclosure provides a microorganism including at least one of the polypeptide having fructose-C4-epimerase activity, a polynucleotide encoding the polypeptide, and a vector including the polynucleotide.

As used herein, the term "polynucleotide" has an inclusive meaning including DNA and RNA molecules, and a nucleotide that is a basic structural unit in the polynucleotide may include not only a natural nucleotide but also an analogue in which a sugar or a base is modified. (Scheit, Nucleotide Analogs, John Wiley, New York (1980); Uhlman and Peyman, Chemical Reviews, 90:543-584 (1990)).

The polynucleotide may be a polynucleotide encoding a polypeptide having an amino acid sequence having at least 85% identity with SEQ ID NO: 1 according to the present disclosure or a polynucleotide encoding a polypeptide having fructose-C4-epimerase activity and 70%, 80%, 85%, 90%, 95%, 96%, 97%, 98%, or 99% homology with the polypeptide according to the present disclosure. Particularly, the polynucleotide encoding the polypeptide having fructose-C4-epimerase activity and including an amino acid sequence having at least 85% identity with SEQ ID NO: 1 may be a polynucleotide having at least 70%, 80%, 85%, 90%, 95%, 96%, 97%, 98%, 99%, or 100% homology or identity with the nucleotide sequence of SEQ ID NO: 2.

In addition, it is obvious that the polynucleotide includes any polynucleotide translated into the protein including the amino acid sequence of SEQ ID NO: 1 and a protein having homology or identity therewith by codon degeneracy. Alternately, the polynucleotide may include any probe prepared from known gene sequences, e.g., a polynucleotide sequence hybridized with a sequence entirely or partially complementary to the nucleotide sequence under stringent conditions to encode the protein having the activity of the protein having the amino acid sequence of SEQ ID NO: 1, without limitation. The term "stringent conditions" refers to conditions which permit specific hybridization between polynucleotides. Such conditions are disclosed in detail in known documents (e.g., J. Sambrook et al., Molecular Cloning, A Laboratory Manual, $2^{nd}$ Edition, Cold Spring Harbor Laboratory press, Cold Spring Harbor, New York, 1989; F. M. Ausubel et al., Current Protocols in Molecular Biology, John Wiley & Sons, Inc., New York). For example, the conditions may include performing hybridization between genes having a high homology or identity, e.g., a homology or identity of 70% or more, 80% or more, 85% or more, specifically 90% or more, more specifically 95% or more, even more specifically 97% or more, and most specifically 99% or more, without performing hybridization between genes having a homology or identity lower than the above homologies or identities, or performing hybridization once, specifically two or three times, under conventional washing conditions for Southern hybridization at a salt concentration and temperature of 60° C., 1×SSC, and 0.1% SDS, specifically 60° C., 0.1×SSC, 0.1% SDS, and more specifically 68° C., 0.1×SSC, and 0.1% SDS.

Hybridization requires that two polynucleotides have complementary sequences, although bases may mismatch due to stringent conditions of hybridization. The term "complementary" is used to describe the relationship between bases of nucleotides capable of hybridizing with each other. For example, with respect to DNA, adenosine is complementary to thymine, and cytosine is complementary to guanine. Therefore, the present disclosure may include not only substantially similar polynucleotide sequence but also a polynucleotide fragment isolated but complementary to the entire sequence.

Particularly, the polynucleotide having homology or identity may be detected under hybridization conditions including a hybridization process using 55° C. as a Tm value using the above-described conditions. In addition, the Tm value may be 60° C., 63° C., or 65° C., but is not limited thereto, and may be appropriately adjusted by those skilled in the art according to the purpose.

The degree of stringent conditions for hybridizing polynucleotides may depend on lengths of the polynucleotides and degrees of complementarity and parameters are well known in the art.

As used herein, the term "homology" or "identity" refers to relevance between two amino acid sequences or nucleotide sequences and may be expressed as a percentage. The terms "homology" and "identity" may often be used interchangeably.

Sequence homology or identity of conserved polynucleotides or polypeptides may be determined by standard alignment algorithm and default gap penalties established by a program may be used together therewith. Substantially, homologous or identical sequences may hybridize to each other at least about 50%, 60%, 70%, 80%, or 90% or more of the entire sequence or the entire lengths under moderately or highly stringent conditions. In hybridization, a polynucleotide including degenerated codon instead of codon may also be considered.

The homology, similarity, or identity between two polynucleotide or polypeptide sequences may be determined using any computer algorithm known in the art, e.g., "FASTA" program, using default parameters introduced by Pearson et al., (1988) [Proc. Natl. Acad. Sci. USA 85]: 2444. Alternatively, the homology, similarity, or identity may be determined using the Needleman-Wunsch algorithm (Needleman and Wunsch, 1970, J. Mol. Biol. 48: 443-453) as implemented in the Needleman program of the EMBOSS package (EMBOSS: The European Molecular Biology Open Software Suite, Rice et al., 2000, Trends Genet. 16: 276-277) (version 5.0.0 or later) (including GCG program package (Devereux, J., et al, Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). For example, the homology, similarity, or identity may be determined using BLAST, from the National Center for Biotechnology Information database, or ClustalW.

The homology, similarity, or identity between polynucleotides or polypeptides may be determined by comparing sequence information using a GAP computer program as introduced by Needleman et al., (1970), J Mol Biol. 48:443 as disclosed by Smith and Waterman, Adv. Appl. Math (1981) 2:482. Briefly, the GAP program defines similarity as the number of aligned symbols (i.e., nucleotides or amino acids) which are similar, divided by the total number of symbols in a shorter of two sequences. Default parameters for the GAP program may include: (1) a unary comparison matrix (containing a value of 1 for identities and 0 for non-identities) and the weighted comparison matrix of Gribskov, et al., Nucl. Acids Res. 14: 6745 (1986) as described by Schwartz and Dayhoff, eds., Atlas Of Protein Sequence and Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (ora gap open penalty of 10 and a gap extension penalty of 0.5); and (3) no penalty for end gaps. Accordingly, as used herein, the term "homology" or "identity" refers to relevance between sequences.

The microorganism expressing the polypeptide having fructose-C4-epimerase activity, which can be used in the present disclosure, may be a microorganism including at least one of the polypeptide, a polynucleotide encoding the polypeptide, and a vector including the polynucleotide.

The vector may be in a form operably linked to the polynucleotide according to the present disclosure. As used herein, the term "operably linked" refers to an operable linkage between a control sequence for nucleotide expression and a nucleotide sequence encoding a target protein for performing general functions thereof, and this may affect the expression of the nucleotide sequence being encoded. Operable linkage with a vector may be prepared using a genetic recombination technique known in the art, and site-specific DNA cleavage and ligation may be performed using a restriction enzyme, a ligase, and the like, known in the art.

As used herein, the term "vector" refers to any mediator for cloning and/or transferring nucleotides into an organism, e.g., a host cell. A vector may be a replicon to allow for the replication of a fragment combined with another DNA fragment. As used herein, the term "replicon" refers to any genetic unit acting as a self-replicating unit for DNA replication in vivo, i.e., being replicable by self-regulation (e.g., plasmids, phages, cosmids, chromosomes, and viruses). The term "vector", as used herein, may include viral and non-viral mediators for introducing nucleotides into an organism, e.g., a host cell in vitro, ex vivo, or in vivo, and also may include a mini-spherical DNA, a transposon such as Sleeping Beauty (lzsvak et al. J. Mol. Biol. 302:93-102 (2000)), or an artificial chromosome. Examples of common vectors include plasmids, cosmids, viruses, and bacteriophages in natural or recombinant states thereof. For example, as a phage vector or cosmid vector, pWE15, M13, MBL3, MBL4, IXII, ASHII, APII, t10, t11, Charon4A, and Charon21A may be used; and as a plasmid vector, pBR-based, pUC-based, pBluescriptII-based, pGEM-based, pTZ-based, pCL-based, and pET-based vectors may be used. The vector used according to the present disclosure is not particularly limited and any known recombinant vectors may also be used. In addition, the vector may be a recombinant vector further including various antibiotic resistance genes. As used herein, the term "antibiotic resistance gene" refers to a gene having resistance to antibiotics, and cells including this gene may survive even in an environment treated with antibiotics. Therefore, the antibiotic resistance gene may be effectively used as a selective marker fora large-scale production of plasmids in *Escherichia coli* (E. coil). In the present disclosure, the antibiotic resistance gene is not a factor that significantly affects the expression efficiency according to an optimal combination of vectors which is core technology of the present disclosure, and thus any common antibiotic resistance genes may be used as a selective marker without limitation. For example, genes resistant to ampicillin, tetracycline, kanamycin, chloroamphenicol, streptomycin, or neomycin may be used.

The microorganism expressing the polypeptide having fructose-C4-epimerase activity according to the present disclosure may be prepared using a method of introducing a vector including a polynucleotide encoding the enzyme into a host cell. The method of transforming the vector may include any method capable of introducing polynucleotides into cells and may be performed by selecting an appropriate standard technique known in the art. For example, electroporation, calcium phosphate co-precipitation, retroviral infection, microinjection, DEAE-dextran, cationic liposome, and heat shock method may be used, without being limited thereto. According to an embodiment, the microorganism expressing the polypeptide having fructose-C4-epimerase activity of the present disclosure may be a microorganism including fructose-C4-epimerase having an amino acid sequence having at least 85% identity with the SEQ ID NO: 1 or a polynucleotide encoding the enzyme.

The transformed gene may be either in a form inserted into the chromosome of a host cell or in a form located outside the chromosome, as long as the gene is expressed in the host cell. In addition, the gene includes DNA and RNA as a polynucleotide encoding a polypeptide and any gene that may be introduced into a host cell and expressed in the host cell may be used without limitation. For example, the gene may be introduced into the host cell in the form of an expression cassette that is a polynucleotide construct including all of the essential elements required for self-replication. The expression cassette may generally include a promoter operably linked to the gene, a transcription termination signal, a ribosome-binding domain, and a translation termination signal. The expression cassette may be in the form of a recombinant vector capable of self-replication. In addition, the gene may be introduced into the host cell by itself or in the form of a polynucleotide construct and operably linked to a sequence required for the expression in the host cell.

The microorganism according to the present disclosure may include any of the prokaryotic and eukaryotic microorganisms which may include the polynucleotide or the recombinant vector according to the present disclosure and are capable of producing fructose-C4-epimerase according to the present disclosure. Examples of the microorganism may include, but are not limited to, microbial strains belonging to the genus of *Escherichia*, the genus of *Erwinia*, the genus of *Serratia*, the genus of *Providencia*, the genus of *Corynebacteria*, and the genus of *Brevibacteria*, particularly, *E. coli* or *Corynebacterium glutamicum*.

The cultures of the microorganism according to the present disclosure may be prepared by culturing the microorganism according to the preset disclosure in a culture medium. The cultures of the microorganism may be the polypeptide, which has fructose-C4-epimerase activity and includes the amino acid sequence of SEQ ID NO: 1, expressed by the microorganism according to the present disclosure in a state of being in contact with an external substrate, without being limited thereto.

As used herein, the term "culturing" refers to growing the microorganism in an appropriately adjusted environment. In the present disclosure, a culturing process may be performed in an appropriate medium and culturing conditions well-known in the art. The cultivation may be easily used after adjustment according to the microbial strain being selected by one of ordinary skill in the art. The culturing of the microorganism may be performed continuously in a batch process, a continuous process, a fed-batch process, etc. known in the art, but the culturing process is not particularly limited thereto. In particular, with respect to the culturing conditions, the pH may be adjusted to a suitable pH (e.g., pH 5 to 9, preferably pH 7 to 9), by using an appropriate basic compound (e.g., sodium hydroxide, potassium hydroxide, or ammonia) or acidic compound (e.g., phosphoric acid or sulfuric acid). Additionally, during the culturing, an anti-foaming agent, such as fatty acid polyglycol ester, may be used to prevent foam generation. Additionally, an aerobic condition of the culture may be maintained by introducing oxygen or an oxygen-containing gas mixture to the culture, and an anaerobic and microaerobic states of the culture may be maintained by introducing nitrogen, hydrogen, or carbon dioxide gas to the culture without the injection of other gases. The culturing temperature may be maintained in the range of 20° C. to 45° C., and specifically 25° C. to 40° C., without being limited thereto. Additionally, the culturing may be continued until a desired yield of a desired substance is obtained, and specifically for 0.5 hours to 160 hours, but is not limited thereto. Additionally, as the carbon sources to be used in the culture medium, sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid) may be used alone or in combination, without being limited thereto. As the nitrogen sources to be used in the culture medium, nitrogen-containing organic compounds (e.g., peptone, yeast extract, meat juice, malt extract, corn steep liquor, soybean flour, and urea) or inorganic compounds (e.g., ammonium sulfate, ammonium chloride, ammonium phosphate, ammonium carbonate, and ammonium nitrate), and the like may be used alone or in combination, but the nitrogen sources are not limited thereto. As the phosphorus sources to be used in the culture medium, potassium dihydrogen phosphate, dipotassium hydrogen phosphate, sodium-containing salts corresponding thereto, and the like may be used alone or in combination, but the phosphorus sources are not limited thereto. Additionally, metal salts (e.g., magnesium sulfate or iron sulfate), amino acids, vitamins, and the like which are essential growth-promoting materials, may be contained in the culture medium.

The composition for producing tagatose according to the present disclosure may further include fructose.

The composition for producing tagatose according to the present disclosure may include a polypeptide having fructose-C4-epimerase activity and directly converting fructose into tagatose, a microorganism expressing the polypeptide, or cultures of the microorganism. The polypeptide having fructose-C4-epimerase activity or a variant thereof may produce tagatose using fructose as a substrate.

The composition for producing tagatose according to the present disclosure may further include any suitable excipient commonly used in compositions for producing tagatose. Examples of the excipient may include, but are not limited to, a preservative, a humectant, a dispersant, a suspension, a buffer solution, a stabilizer, or an isotonic agent.

The composition for producing tagatose according to the present disclosure may further include a metal. According to an embodiment of the present disclosure, the metal may be a metal having a divalent cation. Particularly, the metal according to the present disclosure may be nickel (Ni), magnesium (Mg), or manganese (Mn). More particularly, the metal according to the present disclosure may be a metal ion or a metal salt. More particularly, the metal salt may be $MgSO_4$, $NiSO_4$, $NiCl_2$, $MgCl_2$, $MnCl_2$, or $MnSO_4$.

Another aspect of the present disclosure provides a method of preparing tagatose including converting fructose into tagatose by contacting the composition with fructose.

According to an embodiment, the polypeptide having the fructose-C4-epimerase may include an amino acid sequence having at least 85% identity with SEQ ID NO: 1.

According to an embodiment, the contacting of the present disclosure may be performed under the conditions including a pH 5.0 to 9.0 and a temperature of 30° C. to 80° C. and/or for 0.5 hours to 48 hours.

Specifically, the contacting according to the present disclosure may be performed at a pH of 6.0 to 9.0 or 7.0 to 9.0. In addition, the contacting according to the present disclosure may be performed at a temperature of 30° C. to 80° C., 35° C. to 80° C., 40° C. to 80° C., 50° C. to 80° C., 30° C. to 70° C., 35° C. to 70° C., 40° C. to 70° C., 45° C. to 70° C., 50° C. to 70° C., 30° C. to 65° C., 35° C. to 65° C., 40° C. to 65° C., 45° C. to 65° C., 50° C. to 65° C., 30° C. to 60° C., 35° C. to 60° C., 40° C. to 60° C., 45° C. to 60° C., or 50° C. to 60° C. In addition, the contacting of the present disclosure may be performed for 0.5 hours to 36 hours, 0.5 hours to 24 hours, 0.5 hours to 12 hours, 0.5 hours to 6 hours, 1 hour to 48 hours, 1 hour to 36 hours, 1 hour to 24 hours, 1 hour to 12 hours, 1 hour to 6 hours, 3 hours to 48 hours, 3 hours to 36 hours, 3 hours to 24 hours, 3 hours to 12 hours, 3 hours to 6 hours, 6 hours to 48 hours, 6 hours to 36 hours, 6 hours to 24 hours, 6 hours to 12 hours, 12 hours to 48 hours, 12 hours to 36 hours, 12 hours to 24 hours, 18 hours to 48 hours, 18 hours to 36 hours, or 18 hours to 30 hours.

According to an embodiment, the contacting of the present disclosure may be performed in the presence of a metal. The metal available therefor is as described above.

The preparation method according to the present disclosure may further include separating and/or purifying the prepared tagatose. The separating and/or purifying may be performed using any method commonly used in the art, for example, but not limited to, dialysis, precipitation, adsorption, electrophoresis, ion exchange chromatography, and fractional crystallization. The purifying may be implemented by using the methods alone or in combination thereof.

In addition, the preparation method according to the present disclosure may further include decoloring and/or desalting the prepared tagatose before or after the separating and/or purifying. By performing decoloring and/or desalting, tagatose having higher quality may be obtained According to another embodiment, the preparation method of the present disclosure may further include crystallizing tagatose after the converting, the separating and/or purifying, or the decoloring and/or desalting. The crystallization of tagatose may be performed by using any crystallization method commonly used in the art. For example, cooling crystallization may be used for crystallizing tagatose.

According to another embodiment, the preparation method of the present disclosure may further include concentrating tagatose before the crystallizing. The concentrating may increase a crystallization efficiency.

According to another embodiment, the preparation method of the present disclosure may further include contacting unreacted fructose with the enzyme according to the present disclosure, the microorganism expressing the enzyme, or the cultures of the microorganism after the separating and/or purifying of tagatose; reusing a solution from which crystals are separated in the separating and/or purifying of tagatose after the crystallizing; or any combination thereof.

Another aspect of the present disclosure provides a use of a polypeptide including an amino acid sequence of SEQ ID NO: 1 or an amino acid sequence having at least 85% homology or identity with SEQ ID NO: 1, as fructose-C4-epimerase.

The amino acid sequence of SEQ ID NO, homology, and identity are as described above.

MODE OF DISCLOSURE

Hereinafter, the present disclosure will be described in more detail with reference to the following examples and experimental example. However, these examples and experimental examples are for illustrative purposes only and are not intended to limit the scope of the present disclosure.

Example 1

Preparation of Recombinant Expression Vector Including Gene of Hypothetical Protein and Transformed Microorganism In order to discover a novel heat-resistant fructose-C4-epimerase, gene information of a hypothetical protein whose function has not been revealed was obtained from *Litorilinea aerophile*, and a vector expressible in *Escherichia coli* (*E. coli*) and a transformed microorganism were prepared.

Specifically, a gene sequence of the hypothetical protein was selected from the gene sequence of *Litorilinea aerophila* registered in The Kyoto Encyclopedia of Genes and Genomes (KEGG) and The National Center for Biotechnology Information (NCBI), and a recombinant vector, pBT7-C-His-CJ_LiA_F4E, including a nucleotide sequence of the protein and expressible in *E. coli* was prepared based on information on an amino acid sequence (SEQ ID NO: 1) and a nucleotide sequence (SEQ ID NO: 2) of the microorganism (Bioneer Corporation, Korea).

*E. coli* BL21(DE3) was transformed by heat shock transformation (Sambrook and Russell: Molecular cloning, 2001) using recombinant vector prepared as described above and then stored frozen in 50% glycerol. The transferred strain was named *E. coli* BL21(DE3)/CJ_LiA_F4E.

Example 2

Preparation and Purification of Protein

To prepare a protein, the transformed stain *E. coli* BL21 (DE3)/CJ_LiA_F4E prepared according to Example 1 was inoculated into a culture tube including an LB liquid medium supplemented with ampicillin as an antibiotic and seed culture thereof was performed at 600 nm in a shaking incubator at 37° C. until an absorbance reached 2.0. A culture solution obtained from the seed culture was inoculated in a culture flask including a liquid medium supplemented with LB and lactose, as a protein expression regulatory factor, to perform main culture. The seed culture and main culture were performed at a stirring speed of 180 rpm and at 37° C. Subsequently, the culture solution was centrifuged at 8,000 rpm at 4° C. for 20 minutes to collect strains. The collected strains were washed twice with a 50 mM Tris-HCl buffer solution (pH 8.0) and resuspended in a 50 mM $NaH_2PO_4$ buffer solution (pH 8.0) including 10 mM imidazole and 300 mM NaCl. The resuspended strains were lysed with a sonicator and centrifuged at 13,000 rpm at 4° C. for 20 minutes, and a supernatant was obtained therefrom. The supernatant was purified by Histidine tag (His-tag) affinity chromatography, and non-specific binding proteins were removed therefrom by flowing a 50 mM $NaH_2PO_4$ buffer solution (pH 8.0) including 20 mM imidazole and 300 mM NaCl in an amount of 10 times as much as that of a filer. Thereafter, the resultant was eluted and purified by further flowing the 50 mM $NaH_2PO_4$ buffer solution (pH 8.0) including 20 mM imidazole and 300 mM NaCl, and then subjected to dialysis using a 50 mM Tris-HCl buffer solution (pH 8.0) to obtain purified enzyme, CJ_LiA_F4E, for analysis of enzyme characteristics.

Example 3

Identification of Fructose-C4-epimerase Activity of Hypothetical Protein and Conversion from Fructose into Tagatose In order to identify whether the recombinant enzyme CJ_LiA_F4E prepared according to Example 2 had fructose-C4-epimerase activity, 50 mM Tris-HCl (pH 8.0), 1 mM $NiSO_4$, and 20 mg/mL CJ_LiA_F4E were added to 30 wt % of fructose and the mixture was reacted at 55° C. for 10 hours.

Quantitative analysis was performed for remaining fructose and produced tagatose by high-performance liquid chromatography (HPLC) after the reaction was terminated. HPLC was performed using a Shodex Sugar SP0810 column kept at 80° C. with water, as a mobile phase, at a flow rate of 1 mL/min (FIG. 1).

As a result of the experiment, a conversion rate from fructose into tagatose by CJ_LiA_F4E was identified as 7.24%.

Therefore, it was confirmed that CJ_LiA_F4E protein according to the present disclosure has fructose-C4-epimerase activity and may be used to prepare tagatose.

Example 4: Identification of Activity of CJ_LiA_F4E according to Temperature

In order to investigate influence of temperature on fructose-C4-epimerase activity of the enzyme CJ_LiA_F4E prepared according to Example 2, 10 mg/mL of CJ_LiA_F4E was added to the 50 mM Tris HCl buffer solution (pH 8.0) including 10 wt % of fructose, and the mixture was reacted at various temperatures, e.g., at 45° C., 50° C., 55° C., 60° C., and 65° C. for 10 hours. Quantitative analysis was performed for tagatose by HPLC after the reaction was terminated.

Figure 2:
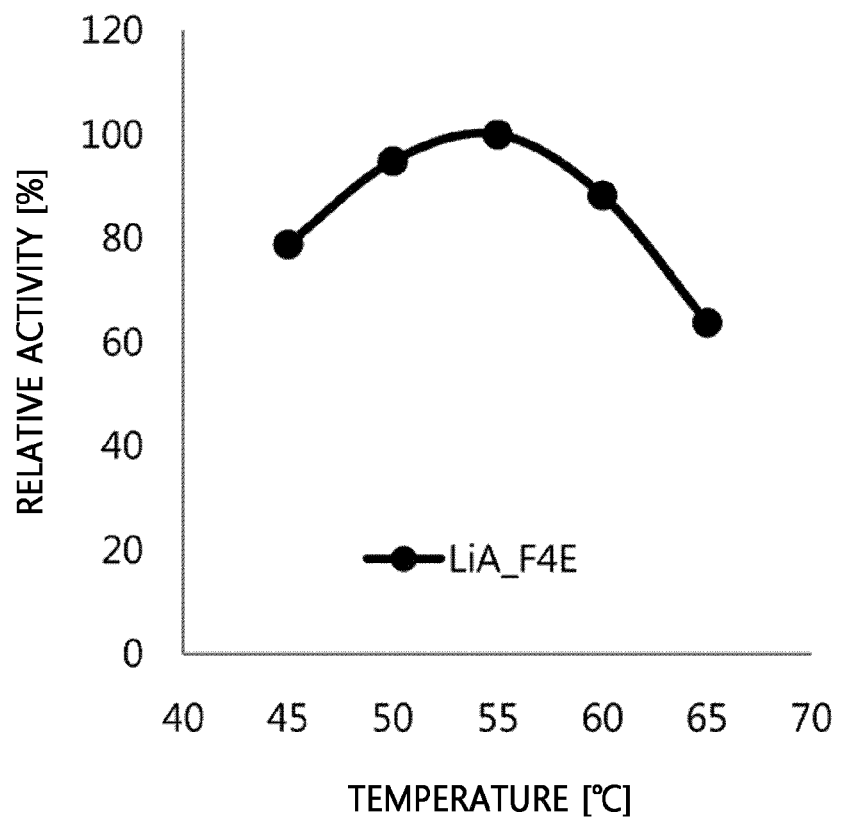
FIG. 2 is a graph illustrating fructose-C4-epimerase activity of CJ_LiA_F4E, as a hypothetical protein, with respect to temperature changes.

As a result of the experiment, CJ_LiA_F4E had a maximum activity at 55° C. and 60% or more of the maximum activity was maintained at all temperature ranges (FIG. 2).

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. The various embodiments disclosed herein are not intended to be limiting, with the true scope and spirit being indicated by the following claims. The present disclosure is to be limited only by the terms of the appended claims, along with the full scope of equivalents to which such claims are entitled.

The invention claimed is:

1. A vector comprising a polynucleotide encoding a polypeptide which has fructose-C4-epimerase activity and comprising an amino acid sequence of SEQ ID NO: 1 or an amino acid sequence having at least 85% identity with SEQ ID NO: 1.

2. A microorganism comprising the vector according to claim 1.

3. The microorganism according to claim 2, wherein the microorganism belongs to the genus of *Escherichia*, the genus *Erwinia*, the genus of *Serrata*, the genus of *Providence*, the genus of *Corynebacteria*, or the genus of *Brevibacteria*.

4. A microorganism comprising a polynucleotide encoding a polypeptide which has fructose-C4-epimerase activity and comprising an amino acid sequence of SEQ ID NO: 1 or an amino acid sequence having at least 85% identity with SEQ ID NO: 1, wherein the microorganism belongs to the genus of *Escherichia*, the genus of *Erwinia*, the genus of *Serratia*, the genus of *Providence*, the genus of *Corynebacteria*, or the genus of *Brevibacteria*.

5. A method of preparing tagatose comprising converting fructose into tagatose by contacting a composition with the fructose, wherein the composition comprises: a polypeptide having fructose-C4-epimerase activity and comprising an amino acid sequence of SEQ ID NO: 1 or an amino acid sequence having at least 85% identity with SEQ ID NO: 1; a microorganism expressing the polypeptide, or cultures of the microorganism.

6. The method according to claim 5, wherein the contacting is performed at a pH of 7.0 to 9.0 and a temperature of 40° C. to 80° C. for 0.5 to 24 hours.

7. The method according to claim 5, wherein the contacting is performed in the presence of an ion or salt of a metal.

8. The method according to claim 7, wherein the metal is at least one metal selected from the group consisting of nickel (Ni) magnesium (Mg), and manganese (Mn).

* * * * *